United States Patent [19]
Godfroid et al.

[11] 4,108,910
[45] Aug. 22, 1978

[54] PROCESS FOR THE STABILIZATION OF METHYLENE CHLORIDE

[75] Inventors: Marcel Godfroid, Wavre; Roger Gerkens, Braine-l'Alleud, both of Belgium

[73] Assignee: Solvay & Cie., Brussels, Belgium

[21] Appl. No.: 790,153

[22] Filed: Apr. 22, 1977

[30] Foreign Application Priority Data

May 3, 1976 [BE] Belgium .................................. 17358

[51] Int. Cl.² ............................................. C07C 17/40
[52] U.S. Cl. .............................. 260/652.5 R; 252/388; 252/392; 252/399; 252/407
[58] Field of Search ................. 260/652.5 R; 252/388, 252/399, 392, 407

[56] References Cited

U.S. PATENT DOCUMENTS

| | | | |
|---|---|---|---|
| 3,838,058 | 9/1974 | Beckers | 260/652.5 R |
| 3,887,628 | 6/1975 | Beckers | 260/652.5 R |
| 3,923,912 | 12/1975 | Beckers | 260/652.5 R |

FOREIGN PATENT DOCUMENTS

1,462,255 12/1966 France ............................. 260/652.5 R

*Primary Examiner*—C. Davis
*Attorney, Agent, or Firm*—Spencer & Kaye

[57] ABSTRACT

The invention relates to a process for the stabilization of methylene chloride, in which a mixture of stabilizers comprising at least one vicinal epoxide and at least one aliphatic monoether is added to the methylene chloride.

Methylene chloride so stabilized is particularly suitable for the degreasing of metals in the vapor phase.

15 Claims, No Drawings

PROCESS FOR THE STABILIZATION OF METHYLENE CHLORIDE

The present invention relates to a process for the stabilisation of methylene chloride in order to avoid its decomposition during its storage or during its use. It also relates to the methylene chloride which has been stabilised in accordance with the process.

Methylene chloride is used as a solvent, both cold and hot, for various industrial applications. One particularly important industrial use of this solvent is the degreasing of metals, where it is employed in the vapour phase. Methylene chloride has numerous advantages for this application: it is resistant to oxidation, to hydrolysis and to pyrolysis and in the cold it virtually does not react with aluminum. Furthermore, it is resistant to photochemical decomposition and hence does not cause atmospheric pollution.

However, when methylene chloride is used in metal degreasing operations and more particularly in vapour phase degreasing, it is found that it has the disadvantage of decomposing in the presence of halides of metals such as iron, zinc or aluminum, or of being able to react with the aromatic compounds usually present on the metals to be degreased, in the presence of halides of metals, or of metals such as iron, zinc or aluminium, with formation of hydrochloric acid and of objectionable tarry substances, which makes the methylene chloride unsuitable for re-use.

It has already been proposed to stabilise chlorinated methanes such as methylene chloride by means of various substances such as amylene (U.S. Pat. No. 1,904,450 in the name of DU PONT DE NEMOURS filed on 3.3.1931), phenol (U.S. Pat. No. 2,008,680 in the name of DU PONT DE NEMOURS filed on 3.3.1931), nitrated compounds (British Pat. No. 773,187 filed on 8.12.1955 in the name of FARBWERKE HOECHST AG), dimethoxymethane (Belgian Pat. No. 741,556 filed on 12.11.1969 in the name of DOW CHEMICAL Co) and epoxides (U.S. Pat. No. 2,106,158 in the name of I.G. FARBEN filed on 4.7.1935).

However, these products have the disadvantage of not ensuring sufficient stability of the methylene chloride. In particular, they are incapable of preventing a rapid decomposition of the methylene chloride and the appearance of tars whilst the methylene chloride is being used for vapour phase degreasing of metals.

In effect, the addition of only one stabilising compound is generally insufficient to avoid these disadvantages.

Furthermore, the addition of several stabilising compounds does not always lead to the anticipated result, either because of their incompatibility or because of the fact that excessively large amounts of product are necessary to ensure good stabilisation.

There has now been found in accordance with the present invention, a new combination of stabilisers which exhibits a synergistic effect when used for stabilising methylene chloride. This combination has proved very efficient even at low doses.

Accordingly, the present invention relates to a process for the stabilisation of methylene chloride in which a mixture of stabilisers comprising at least one vicinal epoxide and at least one aliphatic monoether is added to the methylene chloride.

Epoxides containing 2 to 5 carbon atoms, which may or may not be substituted by halogens, such as ethylene oxide, propylene oxide, epichlorohydrin, the butene oxides and the pentene oxides are most frequently used as the vicinal epoxide. Epoxypropane and epoxybutane are particularly suitable. Epoxypropane has proved particuarly appropriate.

Monoethers containing from 2 to 7 carbon atoms, which may or may not be saturated and may or may not be substituted by halogens are most frequently used as the aliphatic monoether; examples are allyl ethyl ether, allyl isopropyl ether, allyl methyl ether, allyl propyl ether, butyl vinyl ether, butyl ethyl ether, sec.-butyl ethyl ether, tert.-butyl ethyl ether, butyl 2'-chloroethyl ether, butyl methyl ether, sec.-butyl methyl ether, 2-methyl-sec.-butyl methyl ether, tert.-butyl methyl ether, 3-methyl-butyl methyl ether, diallyl ether, diethyl ether, divinyl ether, 1-chlorodiethyl ether, 1,2'-dichlorodiethyl ether, diisopropyl ether, chlorodimethyl ether, dipropyl ether, 1,3-dichlorodipropyl ether, vinyl ethyl ether, vinyl isobutyl ether, vinyl isopropyl ether, vinyl methyl ether, ethyl isobutyl ether, ethyl isopropyl ether, ethyl methyl ether, 1-chloroethyl methyl ether, ethyl chloromethyl ether, 2-chloroethyl methyl ether, 2-chloroethyl pentyl ether, ethyl propyl ether, isobutyl methyl ether, isopropyl methyl ether, isopropyl propyl ether and methyl propyl ether.

Diethyl ether and vinyl ethyl ether are particularly suitable.

A very effective mixure of stabilisers contains epoxypropane and at least one ether chosen from amongst diethyl ether and vinyl ethyl ether.

The total amount of stabilisers to be employed is generally between 0.001 and 10% and most frequently between 0.002 and 5% by weight of the methylene chloride to be treated. In general, from 0.0005 to 8%, and preferably from 0.001 to 4%, by weight of each of the various types of stabilisers are used, and the stabilisers can be present in very different proportions. The weight ratio epoxide/monoether is in general between 100 and 0.01 and preferably between 20 and 0.05. Higher or lower ratios can however also be suitable.

The doses of the various stabilisers given above are the most generally used doses. Lower doses can be used but they are often less effective. Higher doses can also be used but they are generally not justified and they are of little interest from an economic point of view.

It goes without saying that the process for stabilising methylene chloride by the mixture of stabilisers which forms the subject of the present invention can be combined with the use of one or several other stabilisers which are already known.

The invention can also be applied to the stabilisation of mixtures containing methylene chloride.

The example which follows and which is in no way limiting in character shows the remarkable results obtained according to one embodiment of the invention.

EXAMPLE

The stabilising action of mixtures of stabilisers according to the invention, in improving the resistance of methylene chloride to decomposition in the presence of aluminium chloride, has been demonstrated by a laboratory test developed by the BUNDESANSTALT FUER MATERIALPRUEFUNG (Die Berufsgenossenschaft, April 1975, pages 127–128) (the BAM test).

The test is carried out in a 500 cm$^3$ glass flask equipped with a side attachment which allows the introduction of a thermocouple, and a second, CLAISEN, attachment which allows the introduction of water into the flask in case of a runaway reaction, and a reflux condenser surmounted by a drier packed with anhydrous calcium chloride particles.

100 g of solvent are mixed with 100 g of toluene in the flask. 18 g of aluminium flakes and 0.7 g of aluminium chloride are added. The mixture is brought to the boil. The solvent does not meet the test (NO) if it undergoes exothermic decomposition, with formation of tars, or if it continues to decompose after removal of the source of heat within 18 hours.

If the solvent does not undergo any decomposition within 18 hours, it is considered as having met the test (YES).

Experiments 1R, 2R and 3R were carried out by way of comparison, with methylene chloride stabilised respectively with 1,2-epoxypropane alone, diethyl ether alone and ethyl vinyl ether alone.

Experiments 4 and 5 were carried out with mixtures according to the invention.

The results obtained are summarised in Table I below.

TABLE I

| Experiment | 1R | 2R | 3R | 4 | 5 |
|---|---|---|---|---|---|
| Stabilisers g/l | | | | | |
| 1,2-epoxypropane | 10 | | | 10 | 10 |
| diethyl ether | | 10 | | 10 | |
| ethyl vinyl ether | | | 10 | | 10 |
| resistance to the BAM test | no | no | no | yes | yes |

Examination of the results presented in Table I above shows that when a mixture containing 1,2-epoxypropane and an ether chosen from amongst diethyl ether (experiment 4) and ethyl vinyl ether (experiment 5) is used, a product is obtained which meets the BAM test, whilst if each of these stabilisers is used separately the methylene chloride does not meet the BAM test.

We claim:

1. Process for the stabilisation of methylene chloride, comprising adding a mixture of stabilisers comprising at least one vicinal epoxide and at least one aliphatic monoether to the methylene chloride.

2. Process according to claim 1, wherein the vicinal epoxide is 1,2-epoxypropane.

3. Process according to claim 1 wherein the monoether is diethyl ether.

4. Process according to claim 1 wherein the monoether is ethyl vinyl ether.

5. Process according to claim 1, wherein the total amount of stabilisers used is between 0.001 and 10% by weight of the methylene chloride to be treated.

6. Stabilised methylene chloride obtained in accordance with claim 1.

7. Process according to claim 1, wherein, based on the weight of methylene chloride, the amount of vicinal epoxide is from 0.0005 to 8% and the amount of monoether is from 0.0005 to 8%.

8. Process according to claim 1, wherein the epoxide contains 2 to 5 carbon atoms.

9. A stabilized methylene chloride composition containing as the stabilizer a mixture of stabilizers comprising at least one vicinal epoxide and at least one aliphatic monoether.

10. The composition according to claim 9, wherein the vicinal epoxide is 1,2-epoxypropane.

11. The composition according to claim 9, wherein the monoether is diethyl ether.

12. The composition according to claim 9, wherein the monoether is ethyl vinyl ether.

13. The composition according to claim 9, wherein the total amount of stabilizers used is between 0.001 and 10% by weight of the methylene chloride.

14. The composition according to claim 9, wherein, based on the weight of methylene chloride, the amount of vicinal epoxide is from 0.0005 to 8% and the amount of monoether is from 0.0005 to 8%.

15. The composition according to claim 9, wherein the epoxide contains 2 to 5 carbon atoms.

* * * * *